US010562830B2

(12) United States Patent
Lavenn et al.

(10) Patent No.: US 10,562,830 B2
(45) Date of Patent: Feb. 18, 2020

(54) ACETYLENE REMOVAL FROM LIGHT HYDROCARBON MIXTURES BY METAL-ORGANIC FRAMEWORK EXHIBITING DUAL SIZE AND CHEMICAL SELECTIVITIES

(71) Applicants: L'Air Liquide, Société Anonyme pour l'Etude et l'Exploitation des Procédés Georges Claude, Paris (FR); Kyoto University, Kyoto (JP)

(72) Inventors: Christophe Lavenn, Kyoto (JP); Patrick Ginet, Tsukuba (JP); Susumu Kitagawa, Kyoto (JP); Ryotaro Matsuda, Kyoto (JP)

(73) Assignees: L'Air Liquide, Société Anonyme pour l'Etude et l'Exploitation des Procédés Georges Claude, Paris (FR); Kyoto University, Kyoto (JP)

( * ) Notice: Subject to any disclaimer, the term of this patent is extended or adjusted under 35 U.S.C. 154(b) by 97 days.

(21) Appl. No.: 15/829,067

(22) Filed: Dec. 1, 2017

(65) Prior Publication Data

US 2018/0155258 A1    Jun. 7, 2018

(30) Foreign Application Priority Data

Dec. 2, 2016  (JP) ................................. 2016-235111

(51) Int. Cl.
*C07C 7/12* (2006.01)
*B01D 53/047* (2006.01)
(Continued)

(52) U.S. Cl.
CPC .............. *C07C 7/12* (2013.01); *B01D 53/047* (2013.01); *B01J 20/223* (2013.01); *B01D 53/0454* (2013.01); *B01D 2253/204* (2013.01); *B01D 2256/24* (2013.01); *B01D 2257/7022* (2013.01); *B01D 2259/40007* (2013.01)

(58) Field of Classification Search
None
See application file for complete search history.

(56) References Cited

U.S. PATENT DOCUMENTS

2018/0051048 A1* 2/2018 Fujita .................. C07H 15/203

OTHER PUBLICATIONS

Cui, X., et al., Pore chemistry and size control in hybrid porous materials for acetylene capture from ethylene, Science, May 19, 2016, 9 pages, http://science.sciencemag.org.
(Continued)

*Primary Examiner* — Tam M Nguyen
(74) *Attorney, Agent, or Firm* — Allen E. White

(57) ABSTRACT

The present invention provides a gas separation system and a gas separation method capable of separating various types of hydrocarbon gas with high selectivity, and a gas separation system is for separating one type or more of hydrocarbon gases from mixed gas consisting of two types or more of hydrocarbon gases; having a porous metal-organic complex having pores determined by metal ion-containing planar ligands facing each other and pillar ligands coordinating between the planar ligands, and a controller for controlling at least a pressure of the mixed gas; and in which the pressure is controlled to control adsorption of the hydrocarbon gas to the porous metal-organic complex or desorption thereof from the porous metal-organic complex.

8 Claims, 4 Drawing Sheets

(51) Int. Cl.
 B01J 20/22 (2006.01)
 B01D 53/04 (2006.01)

(56) References Cited

OTHER PUBLICATIONS

Cui, X., et al., Supplementary Materials for Pore chemistry and size control in hybrid porous materials for acetylene capture from ethylene, Science, May 19, 2016, 56 pages.
Kitagawa, S., et al., Chemistry of coordination space of porous coordination polymers, Coordination Chemistry Reviews, 251 (2007) 2490-2509.

* cited by examiner

ACETYLENE REMOVAL FROM LIGHT HYDROCARBON MIXTURES BY METAL-ORGANIC FRAMEWORK EXHIBITING DUAL SIZE AND CHEMICAL SELECTIVITIES

CROSS REFERENCE TO RELATED APPLICATIONS

This application claims the benefit of priority under 35 U.S.C. § 119 (a) and (b) to Japanese Patent Application No. JP2016-235111, filed Dec. 2, 2016, the entire contents of which are incorporated herein by reference.

BACKGROUND OF THE INVENTION

Field of the Invention

The present invention is related to a gas separation system and a gas separation method.

Description of the Related Art

Ethylene is industrially produced by steam cracking or pyrolysis, alongside with acetylene as a by-product at concentrations of about 1%. Ethylene is a major chemical for the production of polymers (Ziegler-Natta reaction types) and of other useful chemicals. Acetylene acts as a major catalyst poison for the Ziegler-Natta catalyst used for the polymerization of ethylene. In addition, the presence of acetylene increases safety issues, because of the formation of explosive metal-acetylides with the polymerization catalyst. Therefore, the production of high-grade ethylene is of high and significant interest for the chemical industries. It is usually admitted that in order to have no significant influence of the acetylene over the polymerization process, acetylene concentration should be of less than few parts per million.

For ethylene purification from acetylene impurities, the use of metal-organic frameworks has been proposed in which copper (II) 4,4'-bipyrridine square grids are connected by inorganic ions ($[SiF_6]^{2-}$) between the grids (Non-Patent Document 1).

PRIOR ART DOCUMENT

Non-Patent Document

Non-Patent Document 1: Cui, X.; Chen, K.; Xing, H.; Yang, Q.; Krishana, R.; Bao, Z.; Wu, H.; Zhou, W.; Dong, X.; Han, Y.; Li, B.; Ren, Q.; Zaworotko, M. J.; Chen, B. Science 2016, 353, 141-4.

SUMMARY OF THE INVENTION

When the metal-organic frameworks are used, a selectivity of about 40 are obtained as an experimental condition. However, the selectivity can be improved. Considering industrial applications, the development is desired of separation and purification of lower hydrocarbon gas which is gaseous at room temperature including the above-described two-component gas. However, such development has not been attempted.

In view of the above-described situation, the present invention provides a gas separation system and a gas separation method capable of separating various types of hydrocarbon gas with high selectivity.

As a result of an extensive investigation, the present inventors have found that the above-described problems can be solved by adopting the following configuration and completed the present invention.

The present invention is a gas separation system for separating one type or more of hydrocarbon gases from mixed gas consisting of two types or more of hydrocarbon gases; including a porous metal-organic complex having pores determined by metal ion-containing planar ligands facing each other and pillar ligands coordinating between the planar ligands, and a controller for controlling at least a pressure of the mixed gas; and in which the pressure is controlled to control adsorption of the hydrocarbon gas to the porous metal-organic complex or desorption thereof from the porous metal-organic complex.

In the gas separation system, a porous metal-organic complex is used as a gas separator (adsorbant) having pores determined by metal ion-containing planar ligands that are facing each other and the pillar ligands coordinating between the planar ligands. The size of the pore can be changed depending on the size (especially, a length) of the pillar ligand coordinating between the planar ligands. Accordingly, an appropriate size of the pore can be prepared according to the type, i.e., size, of the hydrocarbon gas to be separated, and selective separation and adsorption can be possible by so-called molecular sieve effect. The planar ligand containing metal ions is relatively rich in electrons, especially, in order to generate the coordination to the metal ions, and relatively strong polarization is occurring. Because the planar ligands coordinates while facing each other and sandwiching the pillar ligands, the polarized parts are also facing each other. In the case of hydrocarbon gas that is relatively strongly polarized such as acetylene and ethylene, the interaction based on a Van der Waals force occurs between the polarized parts facing each other. As a result, the intake of the polarized hydrocarbon gas into the pore is promoted. The porous metal-organic complex exhibits the selectivity due to the degree of polarization of the hydrocarbon gas that is chemical sieve effect. In the gas separation system, the porous metal-organic complex that exhibits both molecular sieve effect and chemical sieve effect is used to control and promote the adsorption of the hydrocarbon gas to the porous metal-organic complex or the desorption thereof from the porous metal-organic complex by controlling the pressure of the mixed gas, which enables gas separation with high selectivity at relatively low pressure. In addition, not limited to acetylene or ethylene as a target of separation, the gas separation system can be also applied to hydrocarbon gas such as methane, ethane, and propane and industrial applications of the gas separation system can be planed because the size of the pore and the degree of polarization of the planar ligand can be changed according to the type of hydrocarbon gas.

The planar ligand preferably contains a polar structure having an unshared electron pair. Accordingly, the interaction between the planar ligand and the hydrocarbon gas (Van der Waals force) can be increased, and the molecules of the hydrocarbon gas can be effectively incorporated into the pores.

The polar structure is preferably at least one selected from —CO—, —NH—, —N=, —O—, and —CN from the viewpoints of improvement of the interaction between the pillar ligand and the gas to be separated and easiness of the molecular design.

The distance between the polar structures that are facing each other is preferably 6 Å to 15 Å. If the distance between the polar structures (correlates to the size of the pore) is in this range, the separation system can be designed according to the hydrocarbon gas to be separated and the selectivity of gas separation can be improved.

The pillar ligands are preferably represented by any of the following formulas (1) to (4).

[Formula 1]

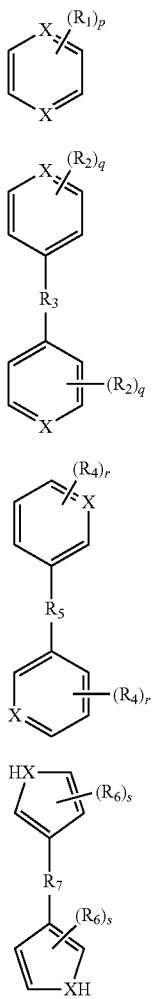

(In the formulas, $R_1$, $R_2$, $R_4$, and $R_6$ are each independently a hydrogen atom, an alkyl group, an alkoxy group, a hydroxy group, a halogen atom, an alkanoyl group, a hydroxyalkyl group, a phenyl group, a phenoxy group, a benzyl group, a phenethyl group, a carboxyl group, a cyano group, or a nitro group. If there are a plurality of $R_1$, $R_2$, $R_4$, and $R_6$ respectively, those may be the same or different.

$R_3$, $R_5$, and $R_7$ are independently a single bond or they represent divalent linking groups containing an unsaturated bond.

P is an integer of 1 to 4, q is an integer of 1 to 4, r is an integer of 1 to 4, and s is an integer of 1 to 3.

X represents N, P, N→O, or P→O.)

If the pillar ligand has the above-described structure, the size of the pore of the porous metal-organic complex can be easily controlled into the desired value, the interaction between the pillar ligand and the hydrocarbon gas can be enhanced, and therefore, the uptake of the hydrocarbon gas into the pore can be further accelerated.

The mixed gas preferably contains hydrocarbon gases of which pKa values are different by 10 or more to each other. If the pKa values of the hydrogen atoms in the hydrocarbon gas molecule differs from each other by 10 or more, the difference of the degree of polarization in the hydrocarbon gas becomes large and the interaction between each hydrocarbon gas and the porous metal-organic complex differs, which enables more effective and selective gas separation.

The hydrocarbon gases are preferably at least two types of gas selected from methane, ethane, ethylene, and acetylene. According to the above-described gas separation system, these hydrocarbon gases that are desired to be separated and purified industrially at high purity can be suitably separated.

The controller preferably performs the following processes: an adsorption process in which the pressure is applied so that the hydrocarbon gases other than the hydrocarbon gases that are the targets of separation can be adsorbed by the porous metal-organic complex, and a desorption process in which the pressure is reduced so that the adsorbed hydrocarbon gases are desorbed gradually from the porous metal-organic complex. In the adsorption process, the hydrocarbon gases having a relatively large molecular size can be separated and collected while allowing the hydrocarbon gases having a relatively small molecular size that fits the size of the pore to be incorporated into the porous metal-organic complex mainly by molecular sieve effect. Even when the mixed gas contains only the hydrocarbon gases having a relatively small molecular size, the hydrocarbon gases having a weak interaction with the porous metal-organic complex can be separated and collected while allowing the hydrocarbon gases having a strong interaction to be incorporated into the pores by chemical sieve effect. In the following desorption process, the desorption can be performed in order from a hydrocarbon gas having the smaller interaction (Van der Waals force) with the porous metal-organic complex mainly by chemical sieve effect, which allows various types of hydrocarbon gases to be separated and collected gradually and selectively. Such control enables the separation and collection of various types of hydrocarbon gases conventionally performed in a different separation facility to be performed in the same system, and the productivity can be improved further.

The present invention is related to a gas separation method for separating one type or more of hydrocarbon gases from mixed gas consisting of two types or more of hydrocarbon gases, including a step of preparing a porous metal-organic complex having pores determined by metal ion-containing planar ligands facing each other and pillar ligands coordinating between the planar ligands, and an adsorption step of applying a pressure to the mixed gas so that the hydrocarbon gases other than the hydrocarbon gases that are the targets of separation are adsorbed by the porous metal-organic complex.

Because a prescribed porous metal-organic complex is used having a molecular sieve effect and a chemical sieve effect in the adsorption step of the gas separation method, the hydrocarbon gases having a relatively large molecular size can be separated and collected while allowing the hydrocarbon gases having a relatively small molecular size that fits the size of the pore to be incorporated into the porous metal-organic complex by molecular sieve effect depending on the pressure. Even when the mixed gas contains only the hydrocarbon gases having a relatively small molecular size, the hydrocarbon gases having a weak interaction with the porous metal-organic complex can be separated and collected while allowing the hydrocarbon gases having a strong interaction to be incorporated into the pores by chemical sieve effect.

The gas separation method preferably further includes a desorption step of reducing the pressure of the mixed gas so that the adsorbed hydrocarbon gases are desorbed gradually from the porous metal-organic complex after the adsorption step. In the desorption step, the desorption can be performed in order from a hydrocarbon gas having the smaller interaction (Van der Waals force) with the porous metal-organic complex mainly by chemical sieve effect, which allows various types of hydrocarbon gases to be separated and collected gradually and selectively.

DETAILED DESCRIPTION OF THE PREFERRED EMBODIMENTS

Figure 1:
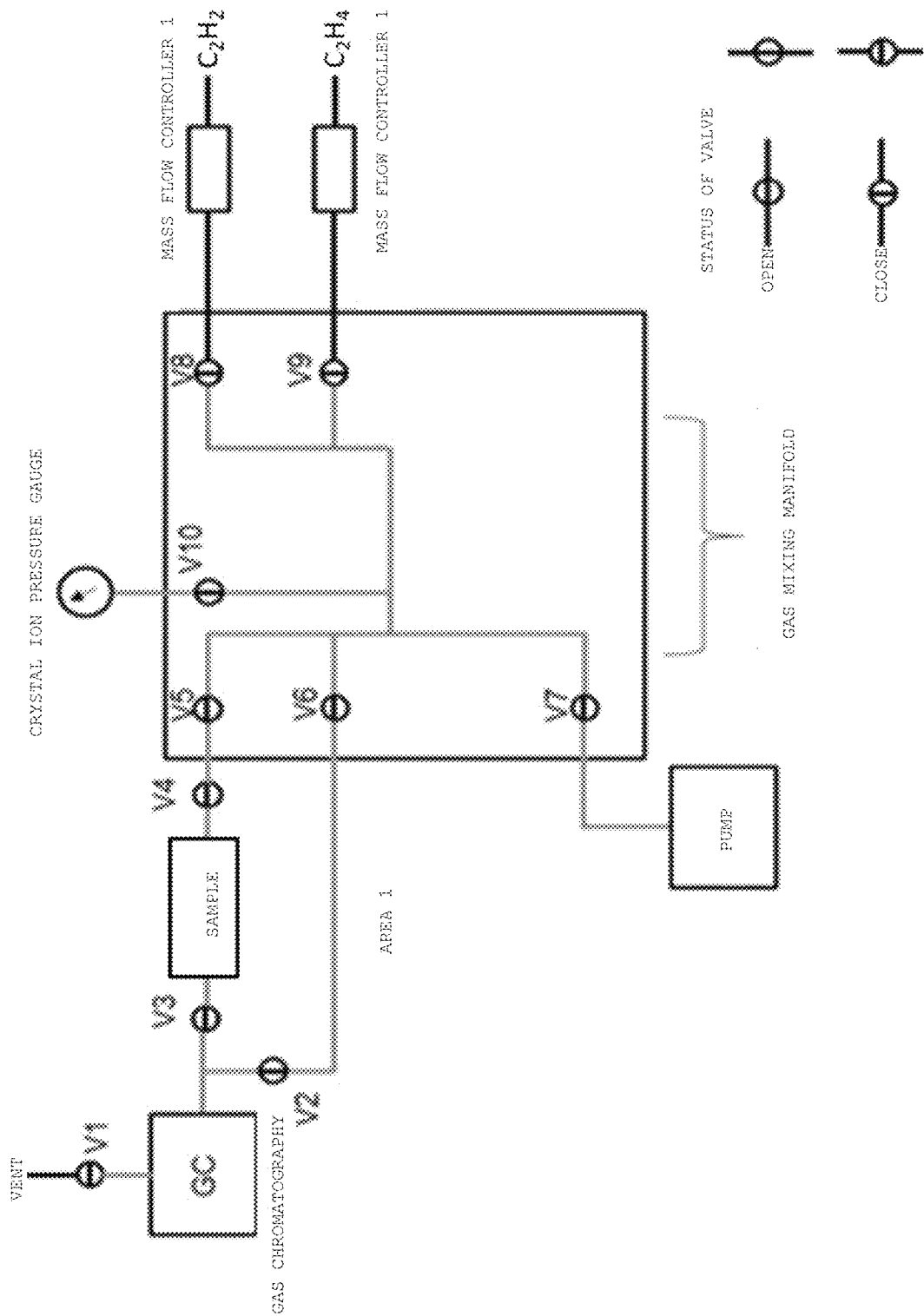
FIG. 1 is an explanatory drawing schematically showing an outline of a gas separation system according to one embodiment of the present invention.

One embodiment of the present invention will be explained using the drawings below. The embodiment explained below is one example of the present invention. The present invention is not limited to this embodiment, and includes various modifications as long as the essential points of the present invention are not changed. All the configurations explained below are not necessarily the essential configurations of the present invention. In a part or the entirety of the drawings, parts that are unnecessary for the explanation are omitted and there are parts that are enlarged or shrunk to make the explanation easy.

<Gas Separation System and Gas Separation Method>

The gas separation system of the present embodiment includes a porous metal-organic complex as a gas separating agent (adsorbant) and a controller for controlling at least a pressure of the mixed gas.

(Porous Metal-Organic Complex)

The porous metal-organic complex has pores determined by metal ion-containing planar ligands facing each other and pillar ligands coordinating between the planar ligands. The planar ligands are preferably nitrogen containing-aromatic polyvalent carboxylic acid ligands, and the pillar ligands are preferably nitrogen or phosphorus containing-aromatic divalent ligands. The nitrogen atoms of the nitrogen containing-aromatic polyvalent carboxylic acid ligand and two carboxylic groups coordinate to the metal ion in a planar manner. The nitrogen or phosphorus containing-aromatic divalent ligands coordinate to the metal ion from the axial direction (direction perpendicular to the plane), and they coordinate so that the planar ligands are crosslinked.

(Metal Ion)

Examples of the metal ion contained in (coordinated by) the planar ligands include a copper ion, an iron ion, a cobalt ion, a nickel ion, palladium ion, a zinc ion, a cadmium ion, a mercury ion, a lead ion, or magnesium ion, preferably a copper ion or a cadmium ion, and more preferably a copper ion.

(Pillar Ligand)

Examples of the nitrogen or phosphorus-containing aromatic divalent ligands that form the pillar ligands include preferably ligands having a nitrogen or phosphorus containing-aromatic ring in which two nitrogen atoms in the aromatic ring are practically positioned in a point symmetry in the molecule, and examples include 4,4'-bipyridyl, 3,3'-bipyridyl, and pyrazine. The nitrogen or phosphorus-containing aromatic divalent ligands may have an arbitrary spacer inserted between two chemical groups as long as coordinating two nitrogen atoms of the aromatic ring are practically positioned in a point symmetry. The pillar ligands are preferably nitrogen-containing aromatic divalent ligands.

The preferred nitrogen or phosphorus containing-aromatic divalent ligands are represented by the following formulas (1) to (4).

[Formula 2]

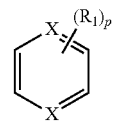

(1)

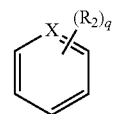

(2)

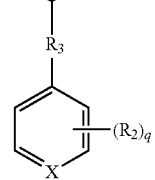

(3)

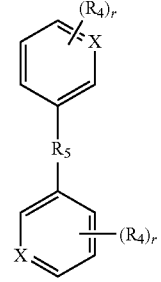

(4)

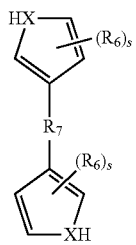

In the formulas, $R_1$, $R_2$, $R_4$, and $R_6$ are each independently a hydrogen atom, an alkyl group, an alkoxy group, a hydroxy group, a halogen atom, an alkanoyl group, a hydroxyalkyl group, a phenyl group, a phenoxy group, a benzyl group, a phenethyl group, a carboxyl group, a cyano group, or a nitro group. If there are a plurality of $R_1$, $R_2$, $R_4$, and $R_6$ respectively, those may be the same or different.

$R_3$, $R_5$, and $R_7$ are independently a single bond or they represent divalent linking groups containing an unsaturated bond. Examples of the divalent linking group include groups containing double bonds such as —N=N— (trans type is preferable), —CH=CH—, —CH=CH—CH=CH—, and —CH=CH—CH=CH—CH=CH— (provided that the double bond is preferably a trans type), groups containing triple bonds such as —C≡C—, —C≡C—C≡C—, and —C≡C—C≡C—C≡C—, and groups represented by the following formulas (11) and (12).

[Formula 3]

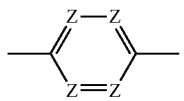
(11)

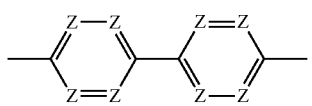
(12)

(In the formulas, Z represents $CR_8$ or N. $R_8$ is a hydrogen atom, an alkyl group, an alkoxy group, a hydroxy group, a halogen atom, an alkanoyl group, a hydroxyalkyl group, a phenyl group, a phenoxy group, a benzyl group, a phenethyl group, a carboxyl group, a cyano group, or a nitro group.)

P is an integer of 1 to 4, q is an integer of 1 to 4, r is an integer of 1 to 4, and s is an integer of 1 to 3.

X represents N, P, N→O, or P→O. X is preferably N (nitrogen atom).

The pillar ligands are especially preferably represented by the following formulas (1-1), (2-1), (2-2), and (2-3). Furthermore, "CPL-1" etc. are the abbreviations of the porous metal-organic complex formed with pyradine-2,3-dicalboxylic acid as planar ligands and the pillar ligands, and they are used through the entire description.

[Formula 4]

(1-1)

CPL-1

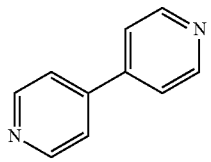
(2-1)

CPL-2

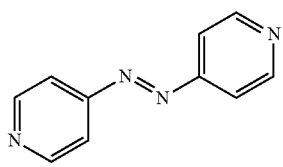
(2-2)

CPL-4

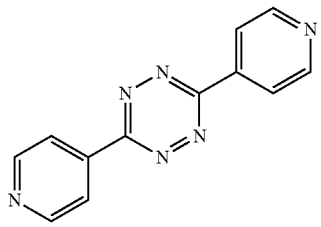
(2-3)

CPL-11

(Planar Ligand)

The planar ligand preferably contains a polar structure having an unshared electron pair. Accordingly, the interaction between the planar ligand and the hydrocarbon gas (Van der Waals force) can be increased, and the molecules of the hydrocarbon gas can be effectively incorporated into the pores.

The polar structure is preferably at least one selected from —CO—, —NH—, —N=, —O—, and —CN, and more preferably —CO— from the viewpoints of improvement of the interaction between the pillar ligand and the gas to be separated and easiness of the molecular design.

The polar structure has a function of enabling selective adsorption of the specific gas based on the chemical conditions. The typical adsorbing site, i.e., the polar structure, is the carbonyl group that does not coordinate to the metal ion. The existence of these free Lewis bases that modify the inside of the pore provides the adsorbing sites that are preferential to the Lewis acid compounds having relatively strong acidity. For example, the protons in acetylene are significantly more acidic than other lower hydrocarbon gas, i.e., partially positively charged, which induces the selectivity of the acetylene molecules.

The nitrogen containing-aromatic polyvalent carboxylic acid ligands forming the planar ligands are compounds in which two or more, preferably two COOH groups are bonded to the aromatic ring in the positions adjacent to one another, i.e., the ortho position. The aromatic ring has a five-membered or six-membered monocyclic skeleton, a dicyclic skeleton or a tricyclic skeleton. Specifically, examples of the skeleton include a monocyclic skeleton, a dicyclic skeleton, and a tricyclic skeleton having one to three nitrogen atoms such as pyrazine, pyridine, pyrrole, thiazol, isothiazol, oxazol, isooxazol, imidazole, pyrazol, pyrimidine, pyridazine, indole, quinoline, isoquinoline, acridine, quinoxaline, quinazoline, phthalazine, and naphthyridine. The nitrogen containing-aromatic polyvalent carboxylic acid ligands preferably have two carboxyl groups at a position adjacent to the nitrogen containing-aromatic ring group and the nitrogen atoms in the aromatic ring, i.e., the ortho position and the meta position viewing from the nitrogen atom. Examples of the preferred aromatic ring include pyrazine, pyridine, and quinoxaline, and these two or more aromatic rings may be linked with a group such as CO, O, and $CH_2$.

The bonding position of two COOH groups with respect to the aromatic ring is preferably the ortho position, i.e., the position at which the COOH groups are adjacent to each other. For example, the nitrogen containing-aromatic polyvalent carboxylic acid ligand is 2,3-pyrazine dicarboxylic acid when the aromatic ring is pyrazine, and 2,3-quinoxaline dicarboxylic acid when the aromatic ring is quinoxaline.

The COOH groups in the nitrogen containing-aromatic polyvalent carboxylic acid ligand may be directly bonded to the aromatic ring, or may be bonded through an appropriate linker (spacer) such as —$CH_2$—, —CO—, —CH(OH)—, and —$CH_2CH_2$—. In the preferred nitrogen containing-aromatic polyvalent carboxylic acid ligand, the COOH groups are directly bonded to the aromatic ring.

The preferred nitrogen containing-aromatic polyvalent carboxylic acid ligands are represented by the following formulas (5) to (9).

[Formula 5]

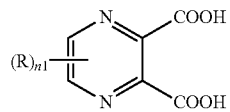

(5)

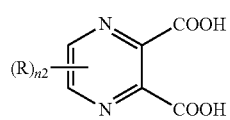

(6)

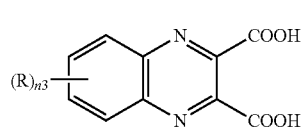

(7)

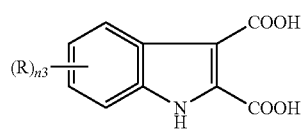

(8)

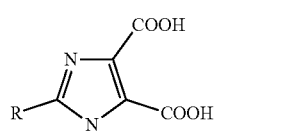

(9)

(In the formulas, $R_{n1}$, $R_{n2}$, and $R_{n3}$ are each independently a hydrogen atom, an alkyl group, an alkoxy group, a hydroxy group, a halogen atom, an alkanoyl group, a hydroxyalkyl group, a phenyl group, a phenoxy group, a benzyl group, a phenethyl group, a carboxyl group, a cyano group, or a nitro group. If there are a plurality of $R_{n1}$, $R_{n2}$, and $R_{n3}$, those may be the same or different.

n1 represents an integer of 1 to 2, n2 represents an integer of 1 to 3, and n3 represents an integer of 1 to 4.)

In the present description, specific examples of the alkyl group include alkyl groups having a straight chain or a branch having 1 to 4 carbon atoms such as a methyl group, an ethyl group, an n-propyl group, an isopropyl group, an n-butyl group, a sec-butyl group, and a tert-butyl group.

Examples of the halogen atom include a fluorine atom, a chlorine atom, a bromine atom, and iodine atom.

Examples of the alkoxy group include alkoxy groups having a straight chain or a branch having 1 to 4 carbon atoms such as a methoxy group, an ethoxy group, an n-propoxy group, an isopropoxy group, an n-butoxy group, a sec-butoxy group, and a tert-butoxy group.

The hydroxyalkyl group is a group in which 1 to 3, preferably 1 to 2, and especially one hydrogen atom in the alkyl group is substituted by the OH group.

Examples of the alkanoyl group include the alkanoyl groups having a direct chain or a branch with 1 to 5 carbon atoms such as a formyl group, an acetyl group, a propionyl group, a butyryl group, and a pivaloyl group.

The distance between the polar structures that are facing each other in the porous metal-organic complex is preferably 6 Å to 15 Å. If the distance between the polar structures (related to the size of the pore) is within this range, the separation system can be designed depending on the type of the hydrocarbon gas to be separated, and the selectivity of gas separation can be improved.

The difference among the lower hydrocarbon gases is a size expressed by a dynamical diameter other than a boiling point and an acidity. As shown in Table 1, the dynamical diameters of the lower hydrocarbon gas are approximate to each other.

TABLE 1

|  | Size (Å³) | Dynamical diameter (Å) | Boiling Point (K) | pKa |
|---|---|---|---|---|
| $C_2H_2$ | 3.32 × 3.34 × 5.70 | 3.3 | 192.3 | 25 |
| $C_2H_4$ | 3.28 × 4.18 × 4.84 | 4.2 | 169.5 | 44 |
| $C_2H_6$ | 3.80 × 4.07 × 4.82 | 4.4 | 184.6 | >50 |
| $CH_4$ | 3.82 × 3.94 × 4.10 | 3.8 | 111.7 | >50 |

In the present embodiment of the invention, the size of the pore and the distance between two free oxygen atoms of the carbonyl group in the pore are preferably adjusted as shown in Table 2.

TABLE 2

|  | Size (Å²) | O—O Distance (Å) |
|---|---|---|
| CPL-1 | 4.0 × 6.0 | 7.9 |
| CPL-2 | 7.2 × 5.6 | 13.7 |
| CPL-4 | 8.6 × 7.3 | 13.7 |
| CPL-11 | 10.2 × 5.9 | 13.8 |

The O—O distance at the cross section of the porous metal-organic complex is compared with the length of acetylene. For example, the O—O distance in CPL-1 that is the pillar ligand is too short for the pore to have two $C_2H_2$ molecules if the hydrogen bond interaction is considered. The O—O distance of the material with larger size of the pores is long enough for the pore to have two molecules. The size of the pore directly influences the gas adsorption. For example, it is confirmed that CPL-1 has one acetylene molecule stored in the material through two hydrogen bonds (one hydrogen bond for each proton), and CPL-1 adsorbs one acetylene molecule per pore (1 mol·mol$^{-1}$) at most. The acetylene storage amount of the CPL having larger pores is 2 mol·mol$^{-1}$ at 298K, and the pores can also adsorb larger hydrocarbon molecules although the selectivity decreases.

(Method for Synthesizing Porous Metal-Organic Complex)

The porous metal-organic complex of the present embodiment can be synthesized by reacting the nitrogen containing-aromatic polyvalent carboxylic acid ligands or their salts, inorganic salts of metal ions, and nitrogen or phosphorous-containing aromatic divalent ligands in a solution in the same method as described in the non-patent document "Kitagawa, S.; Matsuda, R. Coord. Chem. Rev. 2007, 251, 2490." for example.

Figure 4:
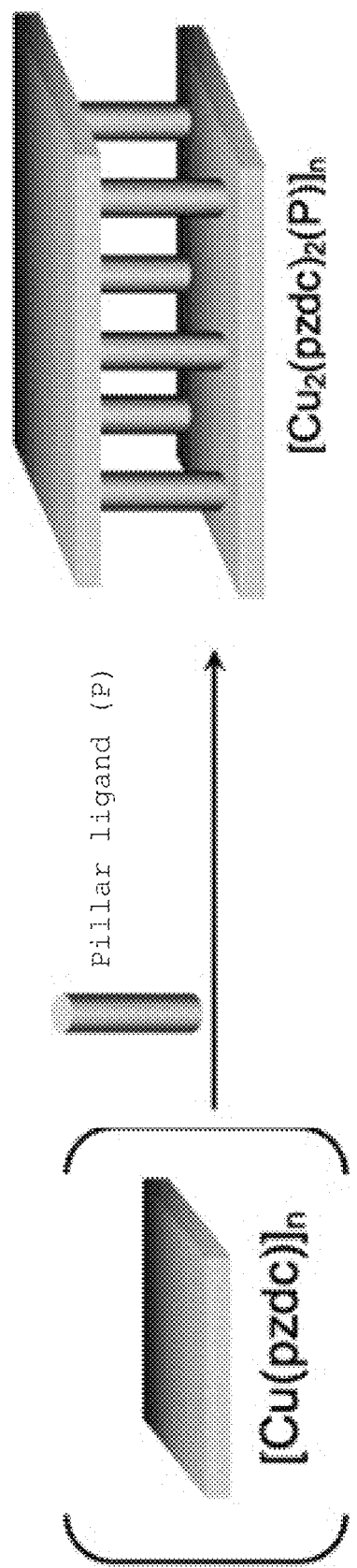
FIG. 4 is a scheme for synthesizing the porous metal-organic complex in which pyrazine-2,3-dicarboxylic acid (H2pzdc) is used as the planar ligand and a copper ion is used as the metal ion.

The scheme for synthesizing the porous metal-organic complex is schematically represented in FIG. 4 when pyrazine-2,3-dicarboxylic acid (H$_2$pzdc) is used as the planar ligand and a copper ion is used as the metal ion.

Omitted Intentionally (see FIG. 4).

Examples of the solvent used in the production of the porous metal-organic complex of the present embodiment include alcohols such as methanol, ethanol, and propanol; saturated hydrocarbons such as benzene, toluene and xylene; halogenated hydrocarbons such as dichloromethane, chloroform, carbon tetrachloride, and dichloroethane; organic solvents such as acetonitrile, tetrahydrofuran, dioxane, dimethylformamide, formamide, dimethylacetoamide, dimethylimidazolidinone, sulforan, and acetone; and water. These solvents may be used either alone or in combination of two or more types.

The reaction temperature is normally about −20° C. to 180° C., and preferably 0° C. to 150° C.

(Controller)

The controller not described in the drawings controls at least a pressure of the mixed gas. The controller preferably controls a temperature, a flow rate, etc. besides the pressure of the mixed gas. The known calculators such as CPU and MPU can be used as the controller.

In the gas separation system of the present embodiment, the pressure is controlled to control the adsorption of the hydrocarbon gases to the porous metal-organic complex or desorption of the hydrocarbon gases from the porous metal-organic complex. The porous metal-organic complex that exhibits both molecular sieve effect and chemical sieve effect is used to control and promote the adsorption of the hydrocarbon gases to the porous metal-organic complex or desorption of the hydrocarbon gases from the porous metal-organic complex by controlling the pressure of the mixed gas, which enables the gas separation with a high selectivity at a relatively low pressure.

FIG. 1 is an explanatory drawing schematically showing an outline of the gas separation system according to the present embodiment. The typical procedure of the gas separation in the system shown in FIG. 1 is explained below. However, the procedure is not limited to this.

(Pretreatment)

The powder sample of the porous metal-organic complex to be used is set in a cryostat system, the system is evacuated (<10$^{-2}$ Pa), and the sample is heated at 373K for 12 hours. After the sample is heated for 12 hours, the temperature is automatically changed to 298K.

(1) Open V10, V4, V5, and V7.
(2) Turn on the controller to control the pump and the temperature.
(3) After 12 hours, close V4, V5, and V7.
(Mixing Gases)
Mass flow controllers (MFC) 1 and 2 are controlled to prepare the gas mixture having a target composition. The area ratio is traced by gas chromatography.
(4) Open V2, V6, V7, V8, and V9 while MFCs 1 and 2 are turned off, and turn on the pump.
(5) Adjust the pressure to <10$^{-2}$ Pa, turn off the pump, and close V7.
(6) Close V2 and turn on MFCs 1 and 2 to obtain a desired gas flow of the gas mixture, and fill Area 1 with the mixture to a maximum pressure of 1 atm.
(7) Open V1 (venting) to control the gas composition by GC injection.
(8) If the stable composition is obtained, close V6, V8, and V9 and V2 and V1 and turn off MFCs 1 and 2.
(Adsorption Process)
After the gas mixture is prepared, the sample area is connected to the gas mixing area and the adsorption equilibrium is kept for 1 hour.
(9) Open V4 and V5.
(10) After 1 hour, close V4 and V5.
(Characterization of Non-Adsorbing Phase (Separating Gas))
After the equilibrium is kept for 1 hour, the non-adsorbing phase is characterized by gas chromatography.
(11) Open V2, V6, V7, V8, and V9 as a preparation for equilibrium, and turn on the pump.
(12) The pressure is adjusted to <10$^{-2}$ Pa, turn on the pump, and close V2, V6, V7, V8, and V9.
(13) Open V3 and close V3 to perform a gas analysis by GC.

<Gas Separation Method>

The gas separation method according to the present embodiment includes a step of preparing a porous metal-organic complex and an adsorption step. Since the porous metal-organic complex is as explained above, the adsorption step will be explained below.

(Adsorption Step)

In the adsorption step, a pressure is applied to the mixed gas so that the hydrocarbon gases other than the hydrocarbon gases to be separated are adsorbed to the porous metal-organic complex.

Because a prescribed porous metal-organic complex is used having a molecular sieve effect and a chemical sieve effect in the adsorption step of the gas separation method of the present embodiment, the hydrocarbon gases having a relatively large molecular size can be separated and collected while allowing the hydrocarbon gases having a relatively small molecular size that fits the size of the pore to be incorporated into the porous metal-organic complex by molecular sieve effect depending on the pressure. Even when the mixed gas contains only the hydrocarbon gases having a relatively small molecular size, the hydrocarbon gases having a weak interaction with the porous metal-organic complex can be separated and collected while allowing the hydrocarbon gases having a strong interaction to be incorporated into the pores by chemical sieve effect.

The pressure applied to the mixed gas can be set according to the type of the hydrocarbon gas to be separated, preferably 0.05 MPa to 5 MPa, more preferably 0.1 MPa to 3 MPa, further preferably 0.2 MPa to 2 MPa, furthermore preferably 0.3 MPa to 1 MPa, and especially preferably 0.3 MPa to 0.8 MPa.

The temperature of the mixed gas in the adsorption step is not especially limited, and a sufficient separation selectivity can be obtained at room temperature (23° C.).

(Desorption Step)

The gas separation method of the present embodiment preferably further includes a desorption step of reducing the pressure of the mixed gas so that the adsorbed hydrocarbon gases can be desorbed gradually from the porous metal-organic complex after the adsorption step. In the desorption step, the desorption can be performed in order from a hydrocarbon gas having the smaller interaction (Van der Waals force) with the porous metal-organic complex mainly by chemical sieve effect, which allows various types of hydrocarbon gases to be separated and collected gradually and selectively.

The pressure of the mixed gas after reducing the pressure can be set according to the type of the hydrocarbon gas to be desorbed. For example, if the target of desorption is acetylene, the pressure of the mixed gas only needs to be adjusted so that the partial pressure of acetylene is preferably 0.1 kPa to 20 kPa, more preferably 0.5 kPa to 18 kPa, and further preferably 1 kPa to 16 kPa.

The mixed gas preferably contains hydrocarbon gases of which pKa value are different by 10 or more to each other. If the pKa values of the hydrogen atoms in the hydrocarbon gas molecule differs from each other by 10 or more, the difference of the degree of polarization in the hydrocarbon gas becomes large and the interaction between each hydrocarbon gas and the porous metal-organic complex differs, which enables more effective and selective gas separation.

The hydrocarbon gases are preferably at least two types selected from methane, ethane, ethylene, and acetylene. According to the gas separation system of the present embodiment, the hydrocarbon gases that are desired to be separated and purified industrially with high purity can be suitably target to be separated.

In the present embodiment, an activation is preferably performed for recycling the porous metal-organic complex after all hydrocarbon gases are desorbed. Heating, vacuum drawing, or combination of these is preferably used as the activation. The activation temperature is preferably 50° C. to 1500° C. and more preferably 60° C. to 120° C.

Examples

The present invention will be explained more in detail by using examples; however, the present invention is not limited to these examples at all as long as the present invention does not depart from the essential points of the invention.

(Synthesis of Porous Metal-Organic Complex)

The following compounds were used in the synthesis of the porous metal-organic complex. All chemicals and solvents with a commercial quality were purchased and used without further purification.

[Formula 7]

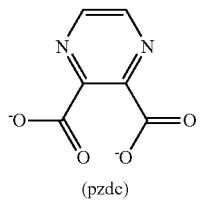

(pzdc)

-continued

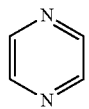

CPL-1

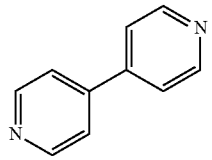

CPL-2

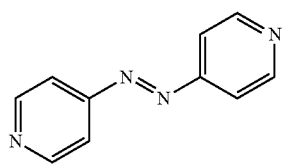

CPL-4

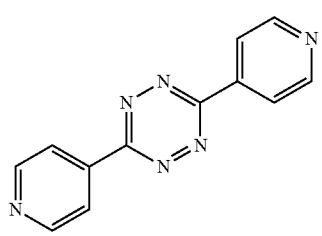

CPL-11

Abbreviation

H$_2$pzdc: pyrazine-2,3-dicarboxylic acid
pzdc: pyrazine-2,3-dicarboxylic acid ion
bpy: 4,4'-bipyridine
azpy: 4,4'-azobispyridine
bptz: 3,6-bis(4-pyridyl)-1,2,4,5-tetrazine (Synthesis of CPL-1)

H$_2$pzdc (1 equivalent, 2 mmol) and NaOH (2 equivalents, 4 mmol) were mixed in a mixture of water and ethanol (50:50, 100 ml total) to prepare a solution of Na$_2$pzdc. This solution was titrated into 100 ml of an aqueous solution containing a copper (II) perchloric acid salt (1 equivalent, 2 mmol) and pyrazine (12.5 equivalents, 25 mmol). After the titration (total of 20 minutes), the reacted substance was stirred at room temperature for 1 day. Then, it was washed three times with water and four times with methanol to collect the precipitant by centrifugal separation and remove the non-reacted chemical species. The powder was dried under a reduced pressure for several hours to synthesize CPL-1.

(Synthesis of CPL-2)

H$_2$pzdc (1 equivalent, 1 mmol) and NaOH (2 equivalents, 2 mmol) were mixed in a mixture of water and ethanol (50:50, 50 ml total) to prepare a solution of Na$_2$pzdc. bpy (0.5 equivalent, 0.5 mmol) was mixed in this solution. This mixture (Na$_2$pzdc+bpy) was titrated into 50 ml of an aqueous solution containing a copper (II) perchloric acid salt (1 equivalent, 1 mmol). After the titration (total of 10 minutes), the reacted substance was stirred at room temperature for 1 day. Then, it was washed three times with water and three times with methanol to collect the precipitant by centrifugal separation and remove the non-reacted chemical species. The powder was dried under a reduced pressure for several hours to synthesize CPL-2.

(Synthesis of CPL-4)

$H_2$pzdc (1 equivalent, 2 mmol) and NaOH (2 equivalents, 4 mmol) were mixed in 100 ml of water to prepare a solution of $Na_2$pzdc. This solution was titrated into a water-ethanol solution (water 50 ml, ethanol 80 ml) containing a copper (II) perchloric acid salt (1 equivalent, 2 mmol) and azpy (12.5 equivalents, 25 mmol). After the titration (total of 15 minutes), the reacted substance was stirred at room temperature for 1 day. Then, it was washed five times with water and four times with methanol to collect the precipitant by centrifugal separation and remove the non-reacted chemical species. The powder was dried under a reduced pressure for several hours to synthesize CPL-4.

(Synthesis of CPL-11)

$H_2$pzdc (1 equivalent, 1 mmol), NaOH (2 equivalents, 2 mmol), and bptz (0.7 equivalent) were mixed in 100 ml of a water-ethanol mixture (50:50) to prepare a solution of [$Na_2$pzdc+bptz]. This solution was titrated into an aqueous solution (100 ml) of a copper (II) perchloric acid salt (1 equivalent, 1 mmol). After the titration (total of 10 minutes), the reacted substance was stirred at room temperature for 1 day. Then, it was washed three times with water and three times with methanol to collect the precipitant by centrifugal separation and remove the non-reacted chemical species. The powder was dried under a reduced pressure for several hours to synthesize CPL-11.

(Characterization of Chemical Species)

All chemical species were characterized by powder x-ray diffraction (pXRD), thermogravimetric analysis (TGA), and adsorption of carbon dioxide gas at 195K. All results matched the theoretical prediction (pXRD/gas adsorption) or the generally known results.

TGA was performed using Rigaku TG8120. About 5 mg to 10 mg of the sample was heated from 25° C. to 500° C. at 10° C./min under nitrogen atmosphere. The pXRD was performed using Rigaku SmartLab X-Ray Diffractometer (40 kV, 40 mA) with CuKα. The pXRD data were recorded from 30° to 60° (2θ) at a scanning speed of 5°/min and a step of 0.01°.

(Gas Isothermal Adsorption)

The gas isothermal adsorption was performed using BEL-SORP-MAX and BELSORP-mini II volume adsorption machine equipped with a cryostat (BELSORP-MAX) and a small cooling device (BELSORP-mini II) for controlling a temperature (manufactured by MicrotracBEL Corp.) The high pressure measurement was performed using BEL-SORP-HP adsorption machine. All samples were degassed at 393K at least for 6 hours before the vacuum adsorption measurement to remove the guest molecules (solvent). The gas isothermal co-adsorption of the binary mixed gas was performed using BELSORP-VC by mixed gas volume adsorption combined with a gas chromatograph (manufactured by MicrotracBEL Corp.) In this evaluation of co-adsorption characteristics, two gases were separately introduced and mixed using a circulating pump. The gas composition was determined from the introduction pressure in which the non-ideality of gas was corrected by using REFPROP. The gas mixture was introduced in the sample chamber so that the gas mixture reached the equilibrium (30 minutes). The total gas adsorption was calculated from the pressure change, and the gas adsorption was determined from the composition of the remaining gas phases using GC. In the GC measurement, the result was obtained by taking an average of values from 7 injections for each data point.

Two gases that were introduced in the gas separation machine used were controlled by a gas selector. The pressure gauge was turned on (open V10) in order to use all hardware.

The gas composition was measured using a gas chromatography machine (GC-2014, manufactured by Shimadzu Corporation) equipped with a Porapack N column (50/80 mesh, SUS tube with a diameter of 3 mm, packed with DVB-EVB ethylene glycol dimethacrylate). The temperature was kept at 90° C. during measurement.

(Isothermal Gas Adsorption and Desorption of Single Component)

The single component isothermal gas adsorption and desorption of acetylene, ethylene, ethane, and methane were performed at 298K using typical materials of the CPL family. The total volume of acetylene, the volume ratio of $C_2H_2/C_2H_4$, and the IAST selectivity represented by the following formula were compared at 298K. The results are shown in Tables 3 and 4.

(IAST Selectivity)

$$S_{ads}=(q_1/q_2)/(p_1/p_2)$$

(in the formula, q is a gas adsorption at a prescribed pressure p.)

TABLE 3

|  | $C_2H_2$ Intake ($cm^3 \cdot g^{-1}$, STP) | $C_2H_4$ Intake ($cm^3 \cdot g^{-1}$, STP) | $C_2H_6$ Intake ($cm^3 \cdot g^{-1}$, STP) | $CH_4$ Intake ($cm^3 \cdot g^{-1}$, STP) |
|---|---|---|---|---|
| CPL-1 | 40.97 | 4.54 | 1.85 | 0.68 |
| CPL-2 | 68.13 | 38.88 | 29.19 | 7.08 |
| CPL-4 | 60.96 | 37.21 | 21.82 | 5.05 |
| CPL-11 | 60.17 | 32.95 | 18.27 | 4.51 |

TABLE 4

|  | $C_2H_2/C_2H_4$ Intake Ratio | $C_2H_2/CH_4$ Intake Ratio | $C_2H_4/C_2H_6$ Intake Ratio | $S_{ads}$ ($C_2H_2/C_2H_4$) (1% $C_2H_2$) | $S_{ads}$ ($C_2H_2/CH_4$) (1% $C_2H_2$) |
|---|---|---|---|---|---|
| CPL-1 | 9.03 | 60.25 | 2.45 | 67.4 | 468.8 |
| CPL-2 | 1.75 | 9.62 | 1.33 | 40.7 | 223 |
| CPL-4 | 1.64 | 12.07 | 1.71 | 11.5 | 83.8 |
| CPL-11 | 1.83 | 13.34 | 1.80 | 15.2 | 110.6 |

(High Pressure Isothermal Gas Adsorption and Desorption of Single Component)

Figures 2A, 2B:
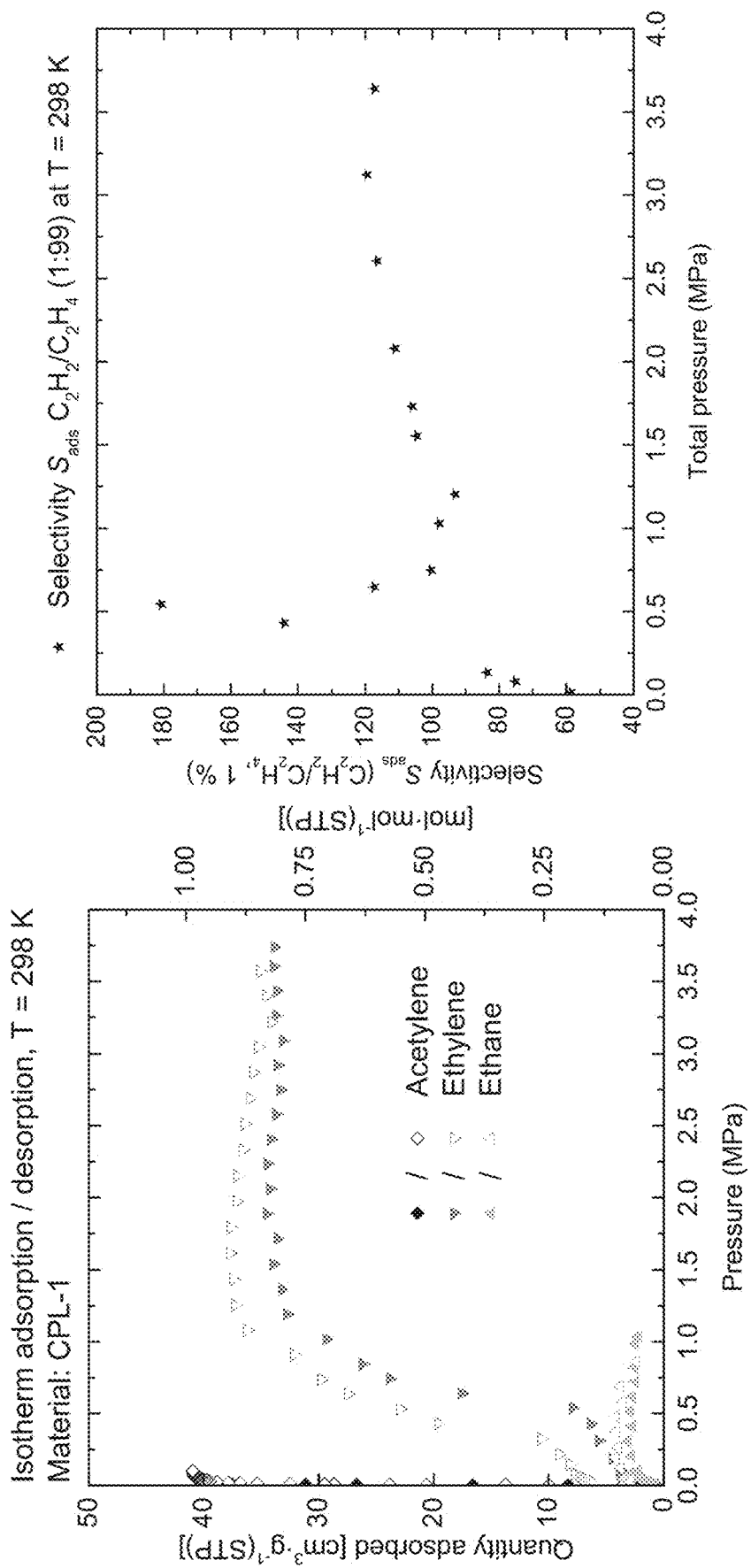
FIG. 2A is a graph showing the gas adsorption (filled) and desorption (open) isothermal curves of acetylene (black diamond), ethylene (gray inverted triangle), and ethane (light gray triangle) at high pressure.
FIG. 2B is a graph showing the corresponding selectivity that is calculated for 1% $C_2H_2$(acetylene) and $C_2H_4$ mixture (Ideal Adsorption Solution Theory: IAST)

The evaluation of the CPL-1 material and the high pressure isothermal gas adsorption and desorption of single component for ethylene ($P_{max}$=3.7 MPa) and ethane ($P_{max}$=1.0 MPa) were performed at 298K, and compared with the acetylene adsorption desorption isothermal curve ($P_{max}$=101.3 kPa). FIG. 2A is a graph showing the gas adsorption (filled) and desorption (open) isothermal curves of acetylene (black diamond), ethylene (gray inverted triangle), and ethane (light gray triangle) at high pressure, and FIG. 2B is a graph showing the corresponding selectivity that is calculated for 1% $C_2H_2$ (acetylene) and $C_2H_4$ mixture (Ideal Adsorption Solution Theory: IAST). The gas adsorption and a corresponding calculated selectivity at a selected pressure for CPL-1 are shown in Table 5.

TABLE 5

| Total pressure (MPa) | $S_{ads}$ ($C_2H_2/CH_4$) (1% $C_2H_2$) |
|---|---|
| 0.1 | 77 |
| 0.54 | 181 |

TABLE 5-continued

| Total pressure (MPa) | $S_{ads}$ ($C_2H_2/CH_4$) (1% $C_2H_2$) |
|---|---|
| 1.03 | 98 |
| 2.08 | 111 |
| 3.64 | 117 |

The applications demonstrated above relate to purification of ethylene from acetylene. It has been found that the porous metal-organic complexes (adsorbants) used are effective due to the combination of the size selectivity (molecular sieve effect) and the chemical selectivity (chemical sieve effect) of the adsorbing materials that were specially designed. The chemical selectivity (chemical sieve effect) is mainly due to a difference of acidities of the hydrocarbon protons because these protons can form a hydrogen bond with the adsorbant.

(Co-Adsorption Test of Ethylene and Ethane)

Figure 3:
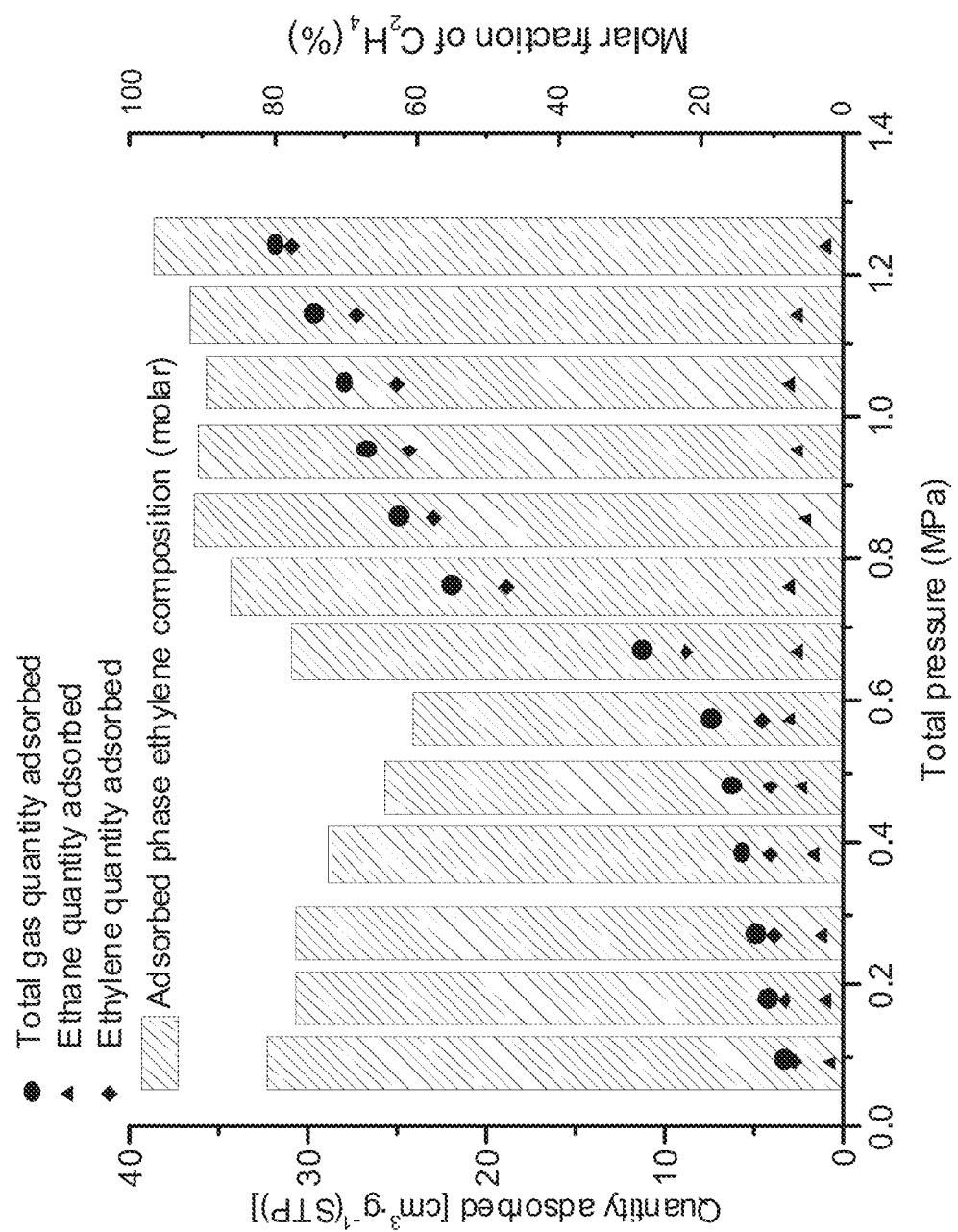
FIG. 3 is a graph showing the total gas adsorption (black circle) of the $C_2H_4$ and $C_2H_6$ mixture adsorbed by CPL-1 adsorbant, the adsorptions of ethylene (diamond) and ethane (black triangle), and the composition determined by gas chromatography (GC) at T=298K.

In addition to the specific capture of acetylene from the ethylene and acetylene mixture, separation of ethylene and ethane has been an important concern. The co-adsorption test of ethylene and ethane was performed on the CPL-1 sample. The results are shown in FIG. 3 and Table 6. FIG. 3 is a graph showing the total gas adsorption (black circle) of the $C_2H_4$ and $C_2H_6$ mixture adsorbed by CPL-1 adsorbant, the adsorptions of ethylene (diamond) and ethane (black triangle), and the composition determined by gas chromatography (GC) at T=298K. Table 6 shows ethylene and ethane adsorptions at a different pressure and corresponding calculated selectivity when the mixed gas (80:20) adsorption was performed on the CPL-1.

TABLE 6

| Pressure (MPa) | Total Intake ($cm^3 \cdot g^{-1}$, STP) | $C_2H_4$ Partial Pressure (MPa) | $C_2H_4$ Intake ($cm^3 \cdot g^{-1}$, STP) | $C_2H_6$ Intake ($cm^3 \cdot g^{-1}$, STP) | Adsorption Phase $C_2H_4$ Molar Ratio | Selectivity |
|---|---|---|---|---|---|---|
| 0.09 | 3.45 | 0.07 | 2.79 | 0.66 | 80.80% | 1.12 |
| 0.27 | 5.13 | 0.21 | 3.96 | 1.17 | 77.10% | 0.9 |
| 0.57 | 7.61 | 0.46 | 4.62 | 2.99 | 60.70% | 0.91 |
| 0.67 | 11.44 | 0.54 | 8.84 | 2.6 | 77.30% | 0.65 |
| 0.76 | 22.1 | 0.61 | 19.04 | 3.06 | 86.10% | 0.45 |
| 0.86 | 25.16 | 0.69 | 22.98 | 2.18 | 91.40% | 0.39 |
| 1.05 | 28.14 | 0.85 | 25.13 | 3.02 | 89.30% | 0.87 |
| 1.24 | 32.02 | 1.01 | 30.99 | 1.03 | 96.80% | 1.6 |

From these tests, it has been proved that the adsorbant can adsorb ethylene at high pressure and ethane is not adsorbed even when ethylene is adsorbed. If the CPL-1 adsorbant is used, the composition of the adsorption phase is over 90% after the pores are opened to $C_2H_4$, and it was proved that ethylene can be effectively captured. Conclusively, by applying a pressure to the mixture so that the partial pressure of $C_2H_4$ becomes over 0.5 MPa at T=298K, ethylene can be captured at high purity. The ethylene with high purity can be collected by reducing a pressure of the adsorbant, and the adsorbant becomes a non-adsorption phase once the substance to be adsorbed is isolated. The desorption pressure should be less than 0.3 MPa (partial pressure of $C_2H_4$) according to the measurement of the purified gas at high pressure.

It is shown that the gas separation can be effectively performed in the three-component system by using the porous metal-organic complexes and applying the technique of controlling pressure shown here. $C_2H_4$ is effectively separated from the $C_2H_4$ and $C_2H_6$ mixture by using the CLP-1 and making the partial pressure of $C_2H_4$ to be over 0.5 MPa, which enables purification of $C_2H_4$ from $C_2H_6$ impurities. The materials described in the present invention can be used to co-adsorb ethylene and acetylene from the three-component mixture of $C_2H_2$, $C_2H_4$, and $C_2H_6$. $C_2H_2$ and $C_2H_4$ have a different release pressure. The release pressure of $C_2H_2$ is about 15 kPa, and that of $C_2H_4$ is about 0.4 MPa to 0.5 MPa. Even if these gases are co-adsorbed at high pressure due to the difference in pressure, the purified acetylene can be collected as long as the partial pressure of acetylene does not become less than 15 kPa.

What is claimed is:

1. A gas separation system for separating one type or more of hydrocarbon gases from a mixed gas consisting of two or more types of hydrocarbon gases, the gas separation system comprising
a porous metal-organic complex having pores determined by metal ion-containing planar ligands facing each other and pillar ligands coordinating between the planar ligands, and
a controller adapted for controlling at least a pressure of the mixed gas; wherein the controller is further adapted to control the pressure of the mixed gas to control an adsorption of the hydrocarbon gas to the porous metal-organic complex or a desorption thereof from the porous metal-organic complex.

2. The gas separation system according to claim 1, wherein the planar ligand contains a polar structure having an unshared electron pair.

3. The gas separation system according to claim 2, wherein the polar structure is at least one selected from —CO—, —NH—, —N=, —O—, and —CN.

4. The gas separation system according to claim 2, wherein a distance between the polar structures facing each other is 6 Å to 15 Å.

5. The gas separation system according to claim 1, wherein the pillar ligands are represented by any one of the following formulas (1) to (4):

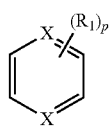

(1)

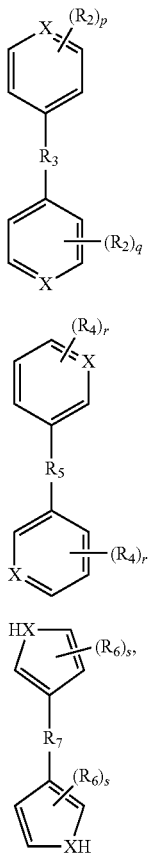

wherein
a) in the formulas, $R_1$, $R_2$, $R_4$, and $R_6$ are each independently a hydrogen atom, an alkyl group, an alkoxy group, a hydroxy group, a halogen atom, an alkanoyl group, a hydroxyalkyl group, a phenyl group, a phenoxy group, a benzyl group, a phenethyl group, a carboxyl group, a cyano group, or a nitro group and further,
b) if there are a plurality of $R_1$, $R_2$, $R_4$, and $R_6$ respectively, those may be the same or different,
c) $R_3$, $R_5$, and $R_7$ are independently a single bond or they represent divalent linking groups containing an unsaturated bond,
d) P is an integer of 1 to 4, q is an integer of 1 to 4, r is an integer of 1 to 4, and s is an integer of 1 to 3, and
e) X represents N, P, N→O, or P→O.

6. The gas separation system according to claim 1, wherein the mixed gas contains hydrocarbon gases of which pKa values are different by 10 or more to each other.

7. The gas separation system according to claim 1, wherein the hydrocarbon gases are at least two types of gas selected from methane, ethane, ethylene, and acetylene.

8. The gas separation system according to claim 1, wherein the controller is adapted to perform the following processes:
an adsorption process in which the pressure is applied so that the hydrocarbon gases other than the hydrocarbon gases that are the targets of separation are adsorbed by the porous metal-organic complex, and
a desorption process in which the pressure is reduced so that the adsorbed hydrocarbon gases are desorbed from the porous metal-organic complex.

* * * * *